(12) United States Patent
Cho, I et al.

(10) Patent No.: US 8,697,420 B2
(45) Date of Patent: Apr. 15, 2014

(54) METHOD FOR PRODUCING CORN GLUTEN HYDROLYSATE AND CORN GLUTEN HYDROLYSATE USING THE SAME

(75) Inventors: Dong Woon Cho, I, Jeollabuk-Do (KR); Dae-Hee Lee, Gyeonggi-Do (KR); Eon Oh, Gyeonggi-Do (KR); Dae Eung Kim, Gyeonggi-Do (KR); Hyun Ah Bae, Seoul (KR); Ji-Hye Kim, Seoul (KR); Byung-Serk Hurh, Seoul (KR)

(73) Assignee: Sempio Foods Company, Seoul (KR)

( * ) Notice: Subject to any disclaimer, the term of this patent is extended or adjusted under 35 U.S.C. 154(b) by 623 days.

(21) Appl. No.: 12/992,531

(22) PCT Filed: May 20, 2009

(86) PCT No.: PCT/KR2009/002667
§ 371 (c)(1),
(2), (4) Date: Nov. 12, 2010

(87) PCT Pub. No.: WO2009/142441
PCT Pub. Date: Nov. 26, 2009

(65) Prior Publication Data
US 2011/0070608 A1    Mar. 24, 2011

(30) Foreign Application Priority Data
May 20, 2008 (KR) .......................... 10-2008-0046582

(51) Int. Cl.
*C12N 1/22* (2006.01)
*A01N 65/00* (2009.01)
(52) U.S. Cl.
USPC .......................................... 435/252; 424/750
(58) Field of Classification Search
None
See application file for complete search history.

(56) References Cited

U.S. PATENT DOCUMENTS

| 4,675,196 A | 6/1987 | Villa et al. |
| 2001/0003593 A1 | 6/2001 | Lim et al. |
| 2003/0022274 A1 | 1/2003 | McNeil |
| 2007/0172914 A1 | 7/2007 | Slabbekoorn et al. |
| 2007/0190130 A1 | 8/2007 | Mark et al. |

FOREIGN PATENT DOCUMENTS

| CN | 1552894 A | 12/2004 |
| EP | 0913097 A1 | 5/1999 |
| EP | 1074632 A1 | 2/2001 |
| JP | 03272694 A | 4/1991 |
| JP | 03204900 A | 9/1991 |
| KR | 100149277 B1 | 6/1998 |
| KR | 100566380 B1 | 3/2006 |

OTHER PUBLICATIONS

Wenying Gu, Mei Wang. "High Fischer Ratio Peptide Mixture—Chapter 4." 3rd International Conference of Food Science and Technology. Copyright 1999. pp. 29-32.
Chen Ding-gang et al., "Development of functional polypeptides in corn gluten meal," Cereals & Oils, pp. 13-14. Date: Mar. 10, 2007.

*Primary Examiner* — Debbie K Ware
(74) *Attorney, Agent, or Firm* — Jansson Munger McKinley & Shape Ltd.

(57) ABSTRACT

Provided is a method for producing corn gluten hydrolysate comprising: (a) separating corn gluten protein by removing carbohydrate, water soluble sugars, inorganic materials and fiber material; (b) preparing corn gluten protein lysate by carrying out acid hydrolysis, enzymatic hydrolysis or natural fermentation; and (c) increasing a content of branch chain amino acid (BCAA) which is included in the hydrolysate by isolating, concentrating, precipitating, desalting and filtering the resultant corn gluten protein lysate. With improved pretreatment and concentration processes as compared with the conventional method, the hydrolysate prepared according to the present invention is rich in amino acids and low-molecular-weight peptides. In particular, free amino acids and branched-chain amino acids (BCAA) are included in large quantity.

15 Claims, No Drawings

METHOD FOR PRODUCING CORN GLUTEN HYDROLYSATE AND CORN GLUTEN HYDROLYSATE USING THE SAME

TECHNICAL FIELD

The present invention relates to a method for producing corn gluten hydrolysate comprising: (a) separating corn gluten protein by removing carbohydrate, water soluble sugars, inorganic materials and fiber material; (b) preparing corn gluten protein lysate by carrying out acid hydrolysis, enzymatic hydrolysis or natural fermentation; and (c) increasing a content of branch chain amino acid (BCAA) which is included in the hydrolysate by isolating, concentrating, precipitating, desalting and filtering the resultant corn gluten protein lysate.

BACKGROUND OF THE INVENTION

Corn contains about 20% w/v of proteins, branched-chain amino acids (BCAA) of which 20-30% w/v based on the proteins. Corn gluten is obtained as a product in the process of isolating sugar components from corn and preparing cornstarch and corn dextrin. In corn gluten, BCAA are included with a content of 20-30 weight %, based on proteins which are included in about 60% w/v.

However, BCAA (leucine, isoleucine and valine) content in the final corn gluten hydrolysate is even lower because of the variation of isoelectric point of the amino acids and the precipitation and breakdown of amino acids caused by chemical and physical factors during the process of producing a hydrolysate from a plant protein-containing raw material including corn gluten. Further, if the content of free amino acids eluted in aqueous solution becomes lower because of low availability of the proteins included in the raw material, BCAA (leucine, isoleucine and valine) content in the final corn gluten hydrolysate becomes even lower.

In addition to the low BCAA content problem in hydrolysis, loss of free amino acids in the following process of treating the aqueous hydrolysate solution may be a problem. In particular, activated carbon usually used for decolorization and deodorization of protein hydrolysate may result in adsorption of large-molecular-weight peptides and proteins, thereby leading to decreased contents of TN, AN (amino nitrogen) and free amino acids including BCAA.

As described above, there exist various factors resulting in the decrease of free amino acid content in the procedures from the preparation of corn gluten hydrolysate to hydrolysis and treatment of the hydrolysate. As a result, the BCAA (leucine, isoleucine and valine) content of the hydrolysate is lower than that of the raw material. Accordingly, in order to increase free amino acid content and BCAA content of the final product, improved pre-treatment and concentration processes of BCAA content of corn gluten are required.

OBJECTS OF THE INVENTION

Therefore, the present invention has been made in view of the above problems, and it is an object of the present invention to solve the technical problems.

Specifically, one object of the present invention is to provide an improved method for producing corn gluten hydrolysate which can increase the a content of branch chain amino acid (BCAA) and free amino acid which are included in the corn gluten hydrolysate than that included in the corn gluten hydrolysate prepared in accordance with existing methods.

Further, another object of the present invention is to provide a corn gluten hydrolysate having rich amino acid and low-molecular-weight peptides, particularly including more free amino acids and BCAA, than corn gluten hydrolysate prepared in accordance with existing methods.

SUMMARY OF THE INVENTION

The present invention has been made in an effort to attain the aforesaid objects. In an aspect, the present invention provides a method for producing corn gluten hydrolysate comprising: (a) separating corn gluten protein by removing carbohydrate, water soluble sugars, inorganic materials and fiber material; (b) preparing corn gluten protein lysate by carrying out acid hydrolysis, enzymatic hydrolysis or natural fermentation; and (c) increasing a content of branch chain amino acid (BCAA) which is included in the hydrolysate by isolating, concentrating, precipitating, desalting and filtering the resultant corn gluten protein lysate.

In an aspect, the present invention provides a corn gluten hydrolysate comprising a large content of free amino acids and BCAA, which is prepared by the method.

In an aspect, the present invention provides a functional food composition comprising the corn gluten hydrolysate as an active ingredient.

In an aspect, the present invention provides a cosmetic food composition comprising the corn gluten hydrolysate as an active ingredient.

In an aspect, the present invention provides a cosmetic composition comprising the corn gluten hydrolysate as an active ingredient.

In an aspect, the present invention provides a pharmaceutical composition comprising the corn gluten hydrolysate as an active ingredient.

DETAILED DESCRIPTION

Hereinafter, reference will be made in detail to various embodiments of the present invention.

As used in the present invention, gluten is an insoluble protein existing in some grains, notably barley, wheat and corn. It may exist as a composite of some proteins. Especially, corn gluten may be obtained by processing wet or dry corn. Since corn gluten is rich in protein content and easily digestible, it is widely used in foods and as additive to foods. Also, it can be used as source of limiting amino acid, because it is rich in methionine.

In the step (a), corn gluten is pre-treated by removing carbohydrate, water soluble sugars, inorganic materials and fiber material and separating corn gluten protein. The corn gluten protein can be isolated with a high purity through the step (a).

Alternatively, the method further comprises a step of heat-treating or steaming the corn gluten before the step (a).

In a preferred embodiment, the heat-treating or steaming process can be carried out by uniformly heat-treating and steaming corn gluten at 110-150° C. for 5-10 minutes, preferably 125-135° C. for 6.5-8.5 minutes using steam and a steaming apparatus, in order to denature protein.

Through the process, protein molecules may be completely denatured. As the conformation structure of the protein molecules is broken down, the amino acid side chains that have been buried inside the protein are exposed, and they may be better contacted by an enzyme.

The removal of the water soluble sugars and the inorganic materials may be carried out by washing the steamed corn gluten with 8-10 times the volume of water in the step (a). To ensure a sufficient removal, it is preferred to warm the water at 50° C. or above and perform shaking at 100 rpm or above. The removal efficiency may be improved as the number of washing increases. However, in order to prevent the loss of water soluble proteins during the washing, the washing may be preferably carried out for 2-3 times.

The fiber materials may be broken down using an enzyme in the step (a). Specifically, the breakdown may be carried out by adding 4-5 times the volume of water to the corn gluten, which has been sufficiently swollen with water and steamed, and then adding a fiber hydrolyzing enzyme.

Preferably, the enzyme may be added in an amount of 0.5-1.0 weight % based on the weight of protein. And, the enzymatic breakdown may be carried out at 40-60° C., pH 4.0-6.0, for 1-2 hours.

The fiber hydrolyzing enzyme may be any complex enzyme that can break down the pectin materials adhered to the plant cell wall, without particular restriction. For example, at least one selected from cellulase, hemicellulase, pectinase and a combination thereof may be used. These complex enzymes are particularly effective in removing the fiber materials included in corn gluten.

Following the breakdown by the fiber hydrolyzing enzyme, corn gluten protein may be isolated further from the corn gluten, using a decanter. Following centrifuge using the decanter, the protein may be purified by re-centrifuging by adding 2 or more times the volume of water to the centrifugate. The purity of the protein may increase as more amount of water is used.

In the step (b), the corn gluten protein is hydrolyzed by carrying out acid hydrolysis, enzymatic hydrolysis or natural fermentation to prepare corn gluten protein lysate.

The acid hydrolysis is a method of hydrolyzing the corn gluten protein by adding an acid and heat-treating. In a preferred embodiment, the acid hydrolysis may be carried out by mixing 35% HCl with the corn gluten protein, adding ⅓ the volume of water based on HCl, and keeping temperature at 105° C. for over 30 hours using steam. After stopping the supply of steam and leaving for over 15 hours, cooling water may be used to lower the temperature to 35° C.

Alternatively, the step (b) may comprise alkalization, following the acid hydrolysis, which may be carried out at 80° C. to pH 9-11, preferably to pH 10, using 50% NaOH. And, following the cooling using cooling water, reverse neutralization using 35% HCl can be carried out to pH 4-6.

The conventional acid hydrolysis using a strong acid is associated with the problem that harmful chlorohydrin compounds, such as 3-MCPD (3-chloro-1,2-propanediol) and 2,3-DCP (2,3-dichloro-1-propanol), are produced during the process. However, through this procedure, the content of 3-MCPD can be reduced down to 0.05 ppm, as compared to 15-20 ppm of the conventional technique.

The enzymatic hydrolysis is a method of hydrolyzing the corn gluten protein by using an enzyme, is advantageous in that it is safer than the acid hydrolysis method and the hydrolysis process can be achieved in short time, and the step (b) comprises hydrolyzing the corn gluten protein by using an enzyme selected from the group consisting of endoenzyme and exoenzyme.

The endoenzyme hydrolyzes the corn gluten protein by acting on an internal part of peptides, and it is not limited if it may be useable enough for hydrolyzing the corn gluten protein, the endoenzyme is for example, one selected from the group consisting of alcalase, protamex and neutrase.

The exoenzyme hydrolyzes the corn gluten protein by acting on the terminal part of peptides, and it is not limited if it may be useable enough for hydrolyzing the corn gluten protein, the exoenzyme is for example, flavourzyme.

In a preferred embodiment, the enzymatic hydrolysis may be carried out using an endoenzyme or using an endoenzyme and an exoenzyme at the same time. The endoenzyme attacks proteins and peptides at random, thereby resulting in a large amount of low-molecular-weight peptides but only a few free amino acids. In contrast, the exoenzyme attacks the ends of proteins or peptides and, thereby, may result in a large amount of free amino acids.

In a preferred embodiment, the enzymatic hydrolysis may be carried out by diluting the corn gluten protein to 20% in water, sterilizing at 90° C. or above for 30-60 minutes, and treating with an endoenzyme under the condition of 40-50° C., pH 5-8. In another preferred embodiment, the enzymatic hydrolysis may be carried out using a combination of an endoenzyme and an exoenzyme.

The enzymatic hydrolysis may be carried out for 48-96 hours. If the concentration of the used enzyme is lower, it is preferred to carry out the enzymatic hydrolysis longer, in order to increase enzyme availability.

However, contamination by microorganisms may be a serious problem in the enzymatic hydrolysis of protein. In order to prevent this problem, a salt-resistant enzyme may be selected and the enzymatic hydrolysis may be carried out under a salt concentration of about 5-10%.

The natural fermentation is a method of hydrolyzing the corn gluten protein by utilizing microorganisms. In a preferred embodiment, the natural fermentation may be carried out by inoculating the corn gluten protein with *Aspergillus oryzae* and culturing to obtain a koji culture. After preparing 20% aqueous solution using the koji culture, a small amount of commercial-grade enzyme may be added. Through this procedure, better protein availability and amino acid elution ratio, comparing to those derived from the enzymatic hydrolysis using commercial-grade enzymes only, may be achieved.

In a preferred embodiment, the natural fermentation may be carried out by inoculating with *Aspergillus oryzae*, culturing at 30° C. for 2 days and adding each 1.0 weight % of an endoenzyme and an exoenzyme based on the total protein of the hydrolysate.

Specifically, the natural fermentation may be carried out by adding warm water of 50° C. so that the concentration of the raw material in the culture becomes 20% (weight-to-weight (w/w)) and the salt concentration becomes 5% (w/w), making the temperature at 45° C., adding each 1.0% (w/w) of an endo-protease and an exo-protease based on the total protein of the raw material, and performing reaction at 45° C. for 72 hours.

Preferably, the pH of the liquid comprising corn gluten may be in the range from 6 to 8. Although the original pH of corn gluten is from 3 to 5, the microorganisms cannot proliferate well at this pH range. Therefore, the pH is controlled to be 6-8, so that the microorganisms can proliferate well. The pH control can be carried out using a commonly used alkaline material. Preferably, NaOH may be used.

Further, it is preferred that the water content of the corn gluten is not greater than 45%. When the water content is greater than 45%, the titer of the protease produced by the microorganisms may decrease.

In the step (c), a content of branch chain amino acid (BCAA) which is included in the hydrolysate is increased by isolating, concentrating, precipitating, desalting and filtering the resultant corn gluten protein lysate.

The isolating process of the step (c) may comprise removing a solid component from the corn gluten protein lysate by using decanter or filter press.

Alternatively, following removing the solid component by using a decanter and a filter press, insoluble components of the corn gluten protein can be removed completely by adding diatomite.

In addition, increasing the content of branch chain amino acid (BCAA) may be achieved by concentrating, adding a precipitation nucleus and controlling pH of the liquid protein lysate.

In concentrating process, the corn gluten protein lysate can be concentrated to more than 50% (v/v) or equal, based on the volume of the corn gluten protein lysate. A precipitation nucleus can be added to the liquid corn gluten protein lysate to lead effective precipitation. The precipitation nucleus may be a standard material for the amino acid desired to precipitate, and is preferably added in an amount of 0.1-0.2% based on volume to attain the desired effect. The pH of the liquid corn gluten protein lysate may be adjusted to pH 5-7.

Following the concentration, a process of precipitation is carried out. The precipitation process may comprise leaving the corn gluten hydrolysate at low temperature, preferably at 30-40° C., for 1-75 hours, preferably for 15-48 hours and separating the precipitation from the liquid gluten protein lysate.

As can be confirmed in the Examples section, the separation of solid components from the liquid using a decanter or a filter press after the leaving, the content of BCAA (leucine, isoleucine and valine) in the solid component can be increased by up to 40%-60%, compared when no leaving process is applied.

The liquid gluten protein lysate may be subjected to desalting for separation of the wanted amino acids, and the desalting can be carried out by electrodialysis.

The electrodialysis is a process of selectively transporting anions or cations using positively and negatively charged ion exchange membranes, thereby separating ions included in aqueous solution. In the process, the pH needs to be adjusted near the isoelectric point of the target amino acid in order to make the amino acid non-polar. During the electrodialysis, electrically neutral amino acids cannot pass through the ion exchange membranes and are concentrated in the dilution tank. On the contrary, charged salts and low-molecular-weight ionic materials pass through the ion exchange membranes and are removed from the dilution tank to the concentration tank. As such, the target amino acids are concentrated in the dilution tank.

The pH of the separated filtrate may be adjusted to pH 1-10, preferably to pH 2-8, because concentrating BCAA is the purpose of this process. Through this process, the pH of the filtrate is adjusted close to the isoelectric point of the amino acids included in BCAA, which is in the range of 3-7. As a result, the amino acids become electrically neutral and solubility thereof in water becomes minimized.

The salts need to be removed as much as possible in order to improve the BCAA content. To this end, the electrodialysis may be finished when the electrical conductivity reaches below 1.0 S/m, preferably below 0.7 S/m.

In the step (c), the concentrated solution collected from the dilution tank may be combined with the solid component precipitated and separated from the liquid protein lysate during the concentration and precipitating processes, and then subjected to the second electrodialysis process.

Further, if a precipitation of another amino acid except BCAA may be derived in the concentrated solution collected from the dilution tank, the liquid protein lysate can be subjected to the second electrodialysis process, after filtering and removing the precipitation of the liquid protein lysate.

At this time, the pH may be adjusted below the pKa values of the BCAA, not close to the isoelectric points, in order to make the BCAA positively charged. Then, through the electrodialysis, the positively charged BCAA can pass through the cation exchange membrane from the dilution tank to the concentration tank and are concentrated there. The electrodialysis may be finished when the electrical conductivity reaches below 0.7 S/m, preferably below 0.5 S/m.

Because the pKa value of the amino acids included in BCAA is in the range of 2-4, the pH may be adjusted to less than 3 or equal, preferably 1-3, in order to make the BCAA positively charged. Then, upon electrodialysis, the positively charged BCAA can pass through the cation exchange membrane from the dilution tank to the concentration tank and are concentrated there, while impurities without electrical charge cannot pass through the ion exchange membrane and remain in the dilution tank.

The resultant solution does not contain insoluble solids and only the target amino acids are charged. Therefore, ultrafiltration (UF) may be carried out.

That is, the BCAA may be more concentrated by utilizing the electrostatic repulsion between the target amino acids and a positively or negatively charged ultrafiltration membrane. Because the BCAA are positively charged in the preceding process, they can be concentrated using a positively charged ultrafiltration membrane.

The membrane used with ultrafiltration may be one made out of polysulfone, polystyrene sulfonate or polysaccharide, and the molecular weight cut-off (MWCO) of the membrane may be not greater than 1,000 (Daltons) in order to increase the electrostatic repulsion between the BCAA and the membrane and the rejection performance of the membrane as much as possible.

The present invention further provides a corn gluten hydrolysate comprising a large content of free amino acids and branched-chain amino acids (BCAA), which is prepared according to the aforesaid preparation method.

The BCAA may be at least one selected from the group consisting of leucine, isoleucine and valine. The content of each leucine, isoleucine and valine is 0 to 99% (w/w) based on the weight of BCAA. BCAA may comprise one or two or three amino acid(s) selected from the group consisting of leucine, isoleucine and valine.

In the hydrolysate, the portion of free amino acids of the total amino acids may be from 60 to 99% (w/w), preferably from 70 to 97% (w/w). And, the portion of BCAA of the free amino acids may be from 10 to 50% (w/w), preferably from 30 to 70% (w/w). Therefore, higher free amino acid content and remarkably higher BCAA content are attained as compared to the conventional hydrolysate (about 12.8% (w/w)).

With high BCAA (e.g., leucine, isoleucine and valine) content, the corn gluten hydrolysate according to the present invention may be used in foods or medicines for providing the functionality of the BCAA.

Therefore, the present invention provides a functional food composition, a food for beauty, a cosmetic composition and a pharmaceutical composition comprising the corn gluten hydrolysate as active ingredient.

The functional food composition or cosmetic food composition may comprise a corn gluten hydrolysate which has a BCAA, for example, corn protein. It may be used as teas such as *oksusu cha* (corn tea); soups; functional drinks and tablets; additives of diet foods, substitute foods or natural foods; additives of baby foods, weaning foods or dried milk; additives of fermented milk, *lactobacillus* drinks, or milk; additives of various drinks; or in various foods such as ice creams, chewing gums, caramels, candies, ice cakes or confectionery; drinks such as soft drinks and alcohol drinks; health functional foods such as vitamin and mineral; and the like.

The cosmetic composition can be formulated into soft cosmetic water, nutritious cosmetic water, nutritious lotion, massage cream, nutritious cream, pack, gel, body cream, body oil or body essence, but are not limited thereto. Other components except essential components can be selected and mixed by the one skilled in the art with any difficulties.

And, the pharmaceutical composition may be used for treatment of including Alzheimer's disease, refreshment of brain fatigue, enhancement of brain function, restoration of memory, and improvement of brain function; treatment of liver diseases including liver cirrhosis and liver cancer, reduction of hangover, promotion of hepatocyte growth, and recovery of liver function; appetite control, weight loss, body fat loss or other anti-obesity purposes; treatment of type 2 diabetes, including insulin control and blood sugar control; or prevention and treatment of hypertension including ACE inhibition.

When the hydrolysate according to the present invention is used in medicine, it may be used as active ingredient and a commonly used inorganic or organic vehicle may be added to prepare an oral or parenteral administration formulation in the form of solid, semisolid or liquid.

Examples of the oral administration formulation may include tablet, pill, granule, soft/hard capsule, powder, fine granule, dispersible powder, emulsion, syrup, pellet, and the like. And, the parenteral administration formulation may include injection, drop, ointment, lotion, spray, suspension, emulsion, suppository, and the like.

A commonly used method may be used in order to prepare the active ingredient of the present invention into such a formulation, and a binder such as gum arabic, cornstarch, microcrystalline cellulose or gelatin, a vehicle such as dicalcium phosphate, lactose or dextrin, a disintegrator such as alginic acid, cornstarch, potato starch or dextrin, a lubricant such as magnesium stearate, a sweetener such as sucrose, stevioside, licorice or saccharin, a flavor such as peppermint, methyl salicylate or fruit flavor, a surfactant, a colorant, a preservative, a stabilizer, a buffer, a suspension agent, or other commonly used adjuvants may be used as desired.

The active ingredient may be in the form of liposome, microparticle, microcapsule, nanocapsule, or the like. In case of a capsule formulation, a liquid or solid vehicle such as polyethylene glycol, cyclodextrin, sugar alcohol or fatty oil may be included.

The pharmaceutical formulation of the hydrolysate of the present invention may be may be administered, for example, orally, parenterally, rectally, topically, transdermally, intravenously, intramuscularly, intra-abdominally, subcutaneously, and the like.

And, the dosage of the active ingredient may be determined by age, sex and body weight of the subject to be treated, particular disease or pathological conditions, severity of disease or pathological conditions, route of administration, and decision by a physician. Those skilled in the art may determine the dosage considering these factors. A usual dosage may be in the range from about 0.001 mg/kg/day to about 2000 mg/kg/day.

EXAMPLES

The following examples illustrate the present invention in more detail, but they are not intended to limit the scope of the present invention.

Example 1

Corn gluten was uniformly heat-treated and steamed for 6.5-8.5 minutes using 125-135° C. of steam to denature protein. After adding 8-10 time the volume of water, shaking at 50° C. and 100 rpm, and washing for 2-3 times, a 20-30% corn gluten solution was prepared (Composition I).

After adjusting the temperature and pH of the solution to 40-60° C. and pH 4.0-6.0, 0.5-1.0% of a fiber hydrolyzing enzyme based on the solid content was added, and enzymatic hydrolysis was carried out for 1-2 hours. After the reaction was completed, a solid content was obtained by centrifuging for 2-3 times (Composition II).

The same volume of corn gluten protein and 35% HCl was combined. Then, ⅓ the volume of water was added and acid hydrolysis was carried out using steam, at 105° C. for over 30 hours. Following residence and cooling, alkalization was carried out at 80° C. to pH 10, using 50% caustic soda. Then, the resultant solution was reverse neutralized by using 35% HCl, to pH 4.9 (Composition III).

After removing solids using a decanter and a filter press and adjusting to pH 5.9-6.1, the composition was concentrated to 50% (v/v). After 20-24 hours of residence at low temperature, the solids were separated from liquid using a decanter or a filter press (Composition IV).

After adjusting the pH of the liquid to pH 5.9-6.1, desalting (electrodialysis) was carried out until the electrical conductivity reached 0.7 S/m (Composition V).

The desalting solution was combined with the solid component of Composition IV and subjected into the second desalting (electrodialysis) by adjusting the pH of the liquid to pH 2.2 (Composition VI).

The liquid from the second desalting (electrodialysis) was prepared into powder following UF through ultrafiltration membrane (Composition VII).

TABLE 1

Protein content of pre-treated corn gluten

| | Total nitrogen content (TN), w/w % | Total protein content, w/w % |
|---|---|---|
| Corn gluten | 10.18 | 63.66 |
| Composition I | 10.90 | 68.18 |
| Composition II | 11.34 | 70.92 |
| Composition VI | 11.20 | 70.12 |

The corn gluten obtained by removing cornstarch from corn by centrifuge included about 60% (w/w) of protein. The major components of the remainder were insoluble components such as cellulose, hemicellulose and lignin. They accounted for about 20-25% (w/w). When corn gluten is heat-treated at high temperature after adding water, the hydrophobic groups of protein are more exposed to the aqueous environment, due to denaturation of the protein. As a result, the molecular structure is broken down, and substances other than protein are released into the aqueous solution. Referring to Table 1, the protein content increased to 68.18% (w/w) by about 5% (w/w) after hydrolysis and heat-treatment. Further, as the cellulose contained in corn gluten is broken down by the fiber hydrolyzing enzyme, the protein content increased to 70.92% (w/w) by about 3-4% (w/w). In the final composition (Composition VII) prepared by treating corn gluten with steam and fiber hydrolyzing enzyme, the protein content increased to 70.12% (w/w) by about 7-8% (w/w).

TABLE 2

Free amino acid content of compositions

| | | Composition III | Composition IV Liquid | Composition IV precipitate | Composition V | Composition VI | Composition VII |
|---|---|---|---|---|---|---|---|
| Free amino acids (weight %, w/w) | ASP | 1.23 | 2.28 | 0.36 | 0.59 | 0.64 | 1.76 |
| | THR | 0.59 | 1.11 | 0.22 | 0.48 | 0.62 | 4.45 |
| | SER | 1.00 | 1.86 | 0.33 | 2.32 | 2.55 | 6.98 |
| | GLU | 3.74 | 7.04 | 1.20 | 3.5 | 2.62 | 5.00 |
| | PRO | 1.69 | 3.54 | 0.58 | 3.03 | 3.43 | 8.21 |
| | GLY | 0.49 | 0.94 | 0.14 | 1.1 | 1.21 | 3.30 |
| | ALA | 1.69 | 3.12 | 0.99 | 3.21 | 3.33 | 3.60 |
| | CYS | 0.05 | 0.11 | 0.00 | 0.02 | 0.02 | 0.05 |
| | VAL | 0.66 | 1.03 | 1.56 | 1.2 | 1.4 | 5.74 |
| | MET | 0.28 | 0.22 | 3.13 | 0.27 | 0.29 | 0.82 |
| | ILE | 0.38 | 0.27 | 4.72 | 1.35 | 2.62 | 8.04 |
| | LEU | 1.12 | 0.50 | 23.74 | 1.95 | 2.25 | 11.9 |
| | TYR | 0.16 | 0.20 | 16.59 | 0.26 | 0.28 | 0.77 |
| | PHE | 0.90 | 0.89 | 8.43 | 1.32 | 1.45 | 3.96 |
| | HIS | 0.18 | 0.36 | 0.53 | 0.48 | 0.52 | 1.43 |
| | LYS | 0.33 | 0.61 | 0.13 | 0.55 | 0.6 | 1.65 |
| | ARG | 0.52 | 1.04 | 0.20 | 0.71 | 0.78 | 2.14 |
| | Total (%) | 15.07 | 25.13 | 62.87 | 22.34 | 24.61 | 69.80 |
| BCAA (weight %, w/w) | | 1.98 | 1.80 | 30.02 | 4.50 | 6.27 | 25.70 |
| BCAA/FAA (%, w/w) | | 14.44 | 7.16 | 47.74 | 20.14 | 25.47 | 36.80 |

The proportion of BCAA of the free amino acids (BCAA/FAA) in the acid hydrolysate of corn gluten (Composition III) was 14.4% (w/w). The precipitate obtained by adjusting the pH of the composition similar to the isoelectric point of BCAA followed by residence had a BCAA/FAA value of 47.74% (w/w). The proportion of BCAA of the free amino acids (BCAA/FAA) in the process of desalting the supernatant mixed with the precipitate increases by about 39.47% comparing to Composition III, and the proportion of BCAA of the free amino acids (BCAA/FAA) in the second desalting process with adjusting pH to less that 2.2 or equal increases by about 76.38%. BCAA/FAA (weight %, w/w) of the final product was 36.80% (w/w), which means that it increased approximately two-fold. FAA content was 69.80% (w/w), which means that 97% of the total amino acids (Table 3: 71.95%, w/w) were broken down into free amino acids.

TABLE 3

| total amino acids (weight %, w/w) | ASP | 4.37 |
|---|---|---|
| | THR | 2.33 |
| | SER | 3.95 |
| | GLU | 14.85 |
| | PRO | 8.45 |
| | GLY | 1.84 |
| | ALA | 6.15 |
| | CYS | 0.55 |
| | VAL | 2.28 |
| | MET | 1.65 |
| | ILE | 1.91 |
| | LEU | 10.86 |
| | TYR | 3.29 |
| | PHE | 4.34 |
| | HIS | 1.66 |
| | LYS | 1.04 |
| | NH3 | 0.37 |
| | ARG | 2.06 |
| | total (%) | 71.95 |

Comparative Example 1

Corn gluten was broken down by acid hydrolysis in the same manner as in Example 1. After removing solids using a decanter and a filter press, desalting (electrodialysis) was carried out until the electrical conductivity reached 0.7 S/m. The desalting solution was prepared into powder following UF through ultrafiltration membrane.

TABLE 4

Protein content of corn gluten hydrolysate prepared without pre-treating

| | Total nitrogen content (TN), w/w % | Total protein content, w/w % |
|---|---|---|
| Corn gluten | 10.18 | 63.66 |
| Composition VII-1 | 8.98 | 56.12 |

As seen in Table 4, the hydrolysate prepared according to the conventional method had lower protein content (56.12%, w/w) than that of the raw material. It is because protein is thermally and chemically unstable. Heating stress and pH change occurring during the processing results in precipitation of protein and lead to decrease of protein content in the final product.

TABLE 5

Free amino acid content of compositions prepared in Comparative Example 1

| | | Composition III-1 | Composition V-1 | Composition VII-1 |
|---|---|---|---|---|
| Free amino acids (weight %, w/w) | ASP | 1.02 | 0.83 | 5.37 |
| | THR | 0.49 | 0.41 | 2.65 |
| | SER | 0.83 | 0.69 | 4.34 |
| | GLU | 3.09 | 2.84 | 18.48 |
| | PRO | 1.40 | 1.23 | 7.63 |
| | GLY | 0.41 | 0.33 | 2.09 |

TABLE 5-continued

Free amino acid content of compositions prepared in Comparative Example 1

|  | Composition III-1 | Composition V-1 | Composition VII-1 |
|---|---|---|---|
| ALA | 1.40 | 1.23 | 7.71 |
| CYS | 0.05 | 0.04 | 0.01 |
| VAL | 0.55 | 0.44 | 2.87 |
| MET | 0.24 | 0.17 | 1.06 |
| ILE | 0.32 | 0.22 | 1.33 |
| LEU | 0.93 | 0.62 | 4.02 |
| TYR | 0.14 | 0.08 | 0.47 |
| PHE | 0.74 | 0.36 | 2.28 |
| HIS | 0.15 | 0.07 | 0.59 |
| LYS | 0.27 | 0.18 | 1.17 |
| ARG | 0.43 | 0.29 | 1.82 |
| Total (%) | 12.46 | 10.03 | 63.88 |
| BCAA (weight %, w/w) | 1.80 | 1.32 | 8.22 |
| BCAA/FAA (%, w/w) | 14.44 | 13.16 | 12.86 |

As in Table 4, BCAA content of the hydrolysate decreased as desalting and UF were carried out. BCAA/FAA of the final powder product was about 12.8% (w/w).

Example 2

As in Example 1, corn gluten was washed (Composition A), and broken down using a fiber hydrolyzing enzyme (Composition B). The resultant solid was prepared into 20% solution, sterilized at 90° C. or above for 30-60 minutes, and subjected to enzymatic hydrolysis for 48-96 hours treating at 40-50° C., pH 5-8 and salt concentration 5-10% with an endoenzyme or a combination of an endoenzyme and an exoenzyme (Composition C). After filtration and concentration, the precipitate was removed (Composition D). Then, following the first desalting (Composition E), the second desalting (Composition F) and UF, the composition was prepared into powder (Composition G).

BCAA/free amino acids content of enzymatic hydrolysate (Example 2) was 10% (w/w) higher than that of acid hydrolysate (Example 1) (compare Composition III and Composition C). After concentration at pH 6.0, precipitate including high concentration of tyrosine was obtained (solid component of Composition D). The final product (Composition G) which was obtained by removal of this precipitate followed by desalting twice and UF, contained about 40% (w/w) of BCAA/free amino acids, which was increased by about 64.7% comparing to that of the enzymatic hydrolysate (Composition C). FAA content was 46.62% (w/w), which means that 70% of the total amino acids (Table 7: 67%, w/w) were broken down into free amino acids unit.

TABLE 7

| total amino acids (weight %, w/w) | ASP | 5.30 |
|---|---|---|
|  | THR | 2.74 |
|  | SER | 4.33 |
|  | GLU | 18.79 |
|  | PRO | 8.84 |
|  | GLY | 2.21 |
|  | ALA | 7.83 |
|  | CYS | 0.39 |
|  | VAL | 3.03 |
|  | MET | 1.19 |
|  | ILE | 1.63 |
|  | LEU | 4.52 |
|  | TYR | 0.40 |
|  | PHE | 2.56 |
|  | HIS | 0.57 |
|  | LYS | 1.34 |
|  | NH3 | 0.19 |
|  | ARG | 1.60 |
|  | total (%) | 67.27 |

Comparative Example 2

Corn gluten was broken down by acid hydrolysis in the same manner as in Example 2. After removing solids using a decanter and a filter press, desalting (electrodialysis) was

TABLE 6

Free amino acid content of compositions prepared in Example 2

|  |  |  |  | Composition D |  |  |  |
|---|---|---|---|---|---|---|---|
|  |  | Composition C | Liquid | precipitate | Composition E | Composition F | Composition G |
| Free amino acids (%, w/w) | ASP | 0.49 | 0.08 | 0.00 | 0.08 | 0.08 | 0.31 |
|  | THR | 0.49 | 0.68 | 0.00 | 0.78 | 0.78 | 3.00 |
|  | SER | 0.64 | 1.51 | 0.00 | 1.52 | 1.33 | 5.83 |
|  | GLU | 2.06 | 0.68 | 0.00 | 0.7 | 0.7 | 2.68 |
|  | PRO | 0.73 | 0.23 | 0.00 | 0.26 | 0.26 | 1.01 |
|  | GLY | 0.41 | 0.12 | 0.00 | 0.13 | 0.15 | 0.49 |
|  | ALA | 1.00 | 1.15 | 0.15 | 1.21 | 1.25 | 4.63 |
|  | CYS | 0.05 | 0.00 | 0.11 | 0 | 0 | 0.00 |
|  | VAL | 0.85 | 0.74 | 0.22 | 1.55 | 1.6 | 5.94 |
|  | MET | 0.24 | 0.22 | 0.26 | 0.25 | 0.25 | 0.97 |
|  | ILE | 0.41 | 0.41 | 0.36 | 1.75 | 1.85 | 6.70 |
|  | LEU | 1.09 | 1.12 | 2.06 | 1.52 | 1.62 | 5.82 |
|  | TYR | 0.14 | 0.72 | 46.53 | 0.13 | 0.13 | 0.50 |
|  | PHE | 0.25 | 1.65 | 6.57 | 1.75 | 1.72 | 6.70 |
|  | HIS | 0.15 | 0.42 | 0.19 | 0.48 | 0.45 | 1.85 |
|  | LYS | 0.14 | 0.23 | 0.03 | 0.05 | 0.04 | 0.19 |
|  | ARG | 0.21 | 0.00 | 0.00 | 0.08 | 0.08 | 0.00 |
|  | 합계 (%) | 9.34 | 9.97 | 56.48 | 12.16 | 12.21 | 46.62 |
| BCAA (%) |  | 2.35 | 2.27 | 2.64 | 4.82 | 5.07 | 18.50 |
| BCAA/FAA (% w/w) |  | 25.2 | 22.76 | 4.67 | 39.63 | 41.52 | 39.60 | carried out until the electrical conductivity reached 0.7 S/m. The desalting solution was prepared into powder following UF through ultrafiltration membrane.

TABLE 8

Free amino acid content of compositions prepared in Comparative Example 2

|  |  | Composition C-1 | Composition E-1 | Composition G-1 |
|---|---|---|---|---|
| Free amino acids (weight %, w/w) | ASP | 0.49 | 0.5 | 2.25 |
|  | THR | 0.49 | 0.5 | 2.27 |
|  | SER | 0.64 | 0.65 | 2.45 |
|  | GLU | 2.06 | 2.1 | 6.58 |
|  | PRO | 0.73 | 0.74 | 3.87 |
|  | GLY | 0.41 | 0.42 | 1.9 |
|  | ALA | 1 | 1.02 | 4.86 |
|  | CYS | 0.05 | 0.05 | 0.23 |
|  | VAL | 0.85 | 0.92 | 3.54 |
|  | MET | 0.24 | 0.25 | 1.11 |
|  | ILE | 0.41 | 0.45 | 3.24 |
|  | LEU | 1.09 | 1.21 | 6.23 |
|  | TYR | 0.14 | 0.14 | 0.65 |
|  | PHE | 0.25 | 0.25 | 1.13 |
|  | HIS | 0.15 | 0.15 | 0.7 |

TABLE 8-continued

Free amino acid content of compositions prepared in Comparative Example 2

|  | Composition C-1 | Composition E-1 | Composition G-1 |
|---|---|---|---|
| LYS | 0.14 | 0.14 | 0.63 |
| ARG | 0.21 | 0.21 | 0.95 |
| Total (%) | 9.34 | 9.71 | 42.6 |
| BCAA (weight %, w/w) | 2.35 | 2.58 | 13 |
| BCAA/FAA (%, w/w) | 25.2 | 26.6 | 30.6 |

BCAA content of the final product was increased by about 5% (w/w) to about 30% (w/w), as compared to the enzyme hydrolysate, as solid contents were concentrated during desalting.

Example 3

Water content of the solid content obtained in Example 1 after hydrolysis of starch and fiber materials was adjusted to 20-40%. After inoculating with *Aspergillus oryzae*, culturing was carried out at 30° C. for 2-3 days. Then, after adjusting the concentration to 20%, enzymatic hydrolysis was carried out for 72 hours under the condition of 5% slat concentration and 45° C. by adding an endoenzyme and an exoenzyme (Composition c). After filtration, removal of the precipitate (Composition d), desalting (Composition e), the second desalting (Composition f) and UF, a powder was prepared (Composition g).

TABLE 9

Free amino acid content of compositions prepared in Example 3

|  |  |  | Composition d |  |  |  |  |
|---|---|---|---|---|---|---|---|
|  |  | Composition c | Liquid | precipitate | Composition e | Composition f | Composition g |
| Free amino acids (weight %, w/w) | ASP | 0.09 | 0.09 | 0.00 | 0.09 | 0.07 | 0.43 |
|  | THR | 0.84 | 0.86 | 0.00 | 0.86 | 0.86 | 4.20 |
|  | SER | 1.63 | 1.67 | 0.00 | 1.67 | 1.62 | 8.16 |
|  | GLU | 1.78 | 1.82 | 0.00 | 1.82 | 1.82 | 3.75 |
|  | PRO | 0.28 | 0.29 | 0.00 | 0.29 | 0.28 | 1.41 |
|  | GLY | 0.14 | 0.14 | 0.23 | 0.14 | 0.14 | 0.69 |
|  | ALA | 1.30 | 1.32 | 0.18 | 1.32 | 1.25 | 6.48 |
|  | CYS | 0.00 | 0.00 | 0.21 | 0.00 | 0 | 0.00 |
|  | VAL | 0.85 | 0.57 | 0.34 | 1.15 | 1.24 | 7.65 |
|  | MET | 0.27 | 0.28 | 0.26 | 0.28 | 0.31 | 1.36 |
|  | ILE | 1.12 | 1.25 | 0.36 | 1.85 | 1.96 | 9.87 |
|  | LEU | 0.59 | 0.58 | 1.56 | 2.30 | 2.65 | 9.57 |
|  | TYR | 0.14 | 0.08 | 50.47 | 0.14 | 0.14 | 0.70 |
|  | PHE | 1.88 | 1.91 | 6.57 | 1.91 | 1.91 | 9.38 |
|  | HIS | 0.52 | 0.53 | 0.19 | 0.53 | 0.53 | 2.59 |
|  | LYS | 0.05 | 0.05 | 0.03 | 0.05 | 0.05 | 0.27 |
|  | ARG | 0.00 | 0.00 | 0.00 | 0.00 | 0 | 0.00 |
| Total (%) |  | 11.47 | 11.70 | 60.40 | 14.39 | 14.83 | 66.51 |
| BCAA (weight %, w/w) |  | 2.56 | 2.40 | 2.26 | 5.30 | 5.85 | 27.09 |
| BCAA/FAA (%, w/w) |  | 22.31 | 20.51 | 3.74 removed | 36.82 | 39.44 | 40.73 |

As in Example 2, at pH 6.0, precipitate including high concentration of tyrosine was obtained. Tyrosine content of the precipitate was 50 weight % (w/w) or higher (precipitate of Composition d). The final product (Composition g) which was obtained by removal of this precipitate followed by desalting twice and UF, contained about 40% (w/w) of BCAA/free amino acids, which was increased by about 76.78% comparing to that of the enzymatic hydrolysate (Composition c). FAA content was 61.52% (w/w), which means that 89% of the total amino acids (Table 10: 75%, w/w) were broken down into free amino acids unit.

TABLE 10

| Total amino acids (weight %, w/w) | ASP | 5.43 |
|---|---|---|
| | THR | 2.81 |
| | SER | 3.06 |
| | GLU | 17.5 |
| | PRO | 6.06 |
| | GLY | 1.85 |
| | ALA | 8.52 |
| | CYS | 0 |
| | VAL | 3.58 |
| | MET | 1.81 |
| | ILE | 3.5 |
| | LEU | 13.8 |
| | TYR | 0 |
| | PHE | 3.47 |
| | HIS | 1.37 |
| | LYS | 1.37 |
| | NH3 | 0.56 |
| | ARG | 0.39 |
| | total (%) | 75% |

Comparative Example 3

The corn gluten of Example 3 was broken down by natural fermentation. After removing solids using a decanter and a filter press, desalting (electrodialysis) was carried out until the electrical conductivity reached 0.7 S/m. The desalting solution was prepared into powder following UF through ultrafiltration membrane.

TABLE 11

Free amino acid content of compositions prepared in Comparative Example 3

| | | Composition c-1 | Composition e-1 | Composition g-1 |
|---|---|---|---|---|
| Free amino acids (weight %, w/w) | ASP | 0.09 | 0.09 | 0.43 |
| | THR | 0.84 | 0.86 | 4.20 |
| | SER | 1.63 | 1.67 | 8.16 |
| | GLU | 1.78 | 1.56 | 5.89 |
| | PRO | 0.28 | 0.29 | 1.41 |
| | GLY | 0.14 | 0.14 | 0.69 |
| | ALA | 1.30 | 1.32 | 6.48 |
| | CYS | 0.00 | 0.00 | 0.00 |
| | VAL | 0.85 | 0.92 | 3.45 |
| | MET | 0.27 | 0.28 | 1.36 |
| | ILE | 1.12 | 1.25 | 6.25 |
| | LEU | 0.59 | 0.72 | 4.35 |
| | TYR | 0.14 | 0.14 | 0.70 |
| | PHE | 1.88 | 1.91 | 9.38 |
| | HIS | 0.52 | 0.53 | 2.59 |
| | LYS | 0.05 | 0.05 | 0.27 |
| | ARG | 0.00 | 0.00 | 0.00 |
| | Total (%) | 11.47 | 11.73 | 55.61 |
| BCAA (weight %, w/w) | | 2.56 | 2.89 | 14.05 |
| BCAA/FAA (%, w/w) | | 22.31 | 24.64 | 25.26 |

As in Comparative Example 2, BCAA content of the final product was increased by about 3% (w/w) to about 25% (w/w), as compared to the enzyme hydrolysate, as solid contents were concentrated during desalting.

Reference throughout this specification to "the embodiment," "the previous embodiment," "one embodiment," "an embodiment," "a preferred embodiment" "another preferred embodiment" or similar language means that a particular feature, structure, or characteristic described in connection with the embodiment is included in at least one embodiment of the present invention. Thus, appearances of the phrases "in the embodiment," "in the previous embodiment," "in one embodiment," "in an embodiment," "in a preferred embodiment," "in another preferred embodiment," and similar language throughout this specification may, but do not necessarily, all refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

While the present invention has been described in connection with certain exemplary or specific embodiments, it is to be understood that the invention is not limited to the disclosed embodiments, but, on the contrary, is intended to cover various modifications, alternatives, modifications and equivalent arrangements as will be apparent to those skilled in the art. Any such changes, modifications, alternatives, modifications, equivalents and the like may be made without departing from the spirit and scope of the invention.

The invention claimed is:

1. A method for producing corn gluten hydrolysate comprising:
    (a) separating corn gluten protein by removing carbohydrate, water soluble sugars, inorganic materials and fiber material;
    (b) preparing corn gluten hydrolysate by carrying out acid hydrolysis, enzymatic hydrolysis or natural fermentation; and
    (c) increasing a content of branch chain amino acid (BCAA) which is included in the hydrolysate by isolating, concentrating, precipitating, desalting and filtering the resultant corn gluten hydrolysate,
    wherein the desalting comprises electrodialysis by adjusting the corn gluten hydrolysate to pH 1-10.

2. The method for producing corn gluten hydrolysate as set forth in claim 1, wherein the step (b) comprises, following the acid hydrolysis, carrying out alkalization to pH 9-11 and then carrying out reverse neutralization through acidification to pH 4-6.

3. The method for producing corn gluten hydrolysate as set forth in claim 1, wherein the enzymatic hydrolysis of the step (b) comprises hydrolyzing the corn gluten protein by using an enzyme selected from the group consisting of endoenzyme and exoenzyme.

4. The method for producing corn gluten hydrolysate as set forth in claim 1, wherein the step (b) comprises hydrolyzing the corn gluten protein by inoculating the corn gluten protein with *Aspergillus oryzae* and adding an enzyme selected from the group consisting of endoenzyme and exoenzyme.

5. The method for producing corn gluten hydrolysate as set forth in claim 1, wherein the concentrating process of the step (c) comprises adding a precipitation nucleus, adjusting the corn gluten hydrolysate to pH 5-7, and separating the precipitation from the livid corn gluten hydrolysate protein lysate.

6. The method for producing corn gluten hydrolysate as set forth in claim 1, wherein the precipitating process of the step (c) comprises leaving the corn gluten hydrolysate at 30-40° C., for 1-75 hours, and separating the precipitation from the corn gluten hydrolysate.

7. The method for producing corn gluten hydrolysate as set forth in claim 1, wherein the desalting process of the step (c) comprises electrodialysis by adjusting the corn gluten hydrolysate to pH 2-8.

8. The method for producing corn gluten hydrolysate as set forth in claim 1, wherein the desalting process of the step (c) further comprises a second desalting process by combining the concentrated corn gluten hydrolysate with the precipitation produced during the concentrating process and the precipitating process.

9. The method for producing corn gluten hydrolysate as set forth in claim 8, wherein the step (c) further comprises removing precipitation consisting of an amino acid except BCAA.

10. The method for producing corn gluten hydrolysate as set forth in claim 8, wherein pH is controlled at less than 3 or equal during the second desalting process.

11. A corn gluten hydrolysate comprising 60-99% (w/w) of free amino acids based on the weight of total amino acids included in the hydrolysate and 30-70% (w/w) of branched-chain amino acids (BCAA) based on the weight of free amino acids, which is prepared by the method as set forth in claim 1.

12. The corn gluten hydrolysate set forth in claim 11, wherein the BCAA are at least one selected from the group consisting of leucine, isoleucine and valine.

13. The corn gluten hydrolysate set forth in claim 12, wherein the content of each leucine, isoleucine and valine is 0 to 99% (w/w) based on the weight of BCAA.

14. The corn gluten hydrolysate set forth in claim 12, wherein the content of each leucine, isoleucine and valine is 1 to 80% (w/w) based on the weight of BCAA.

15. A composition comprising the corn gluten hydrolysate as set forth in claim 11 as an active ingredient.

\* \* \* \* \*

UNITED STATES PATENT AND TRADEMARK OFFICE
CERTIFICATE OF CORRECTION

| | | |
|---|---|---|
| PATENT NO. | : 8,697,420 B2 | Page 1 of 1 |
| APPLICATION NO. | : 12/992531 | |
| DATED | : April 15, 2014 | |
| INVENTOR(S) | : I Cho et al. | |

It is certified that error appears in the above-identified patent and that said Letters Patent is hereby corrected as shown below:

In the Specification

In column 1, line 64, delete the letter "a".

In column 6, line 52, delete duplicate ")".

In column 7, line 10, delete "with" and replace with --without--.

In column 7, line 50, delete duplicate words "may be".

In column 8, line 5, delete "time" and replace with --times--.

In column 14, line 25, delete "slat" and replace with --salt--.

In the Claims

In column 17, line 2, Claim 5, delete "livid".

In column 17, line 2, Claim 5, delete "protein lysate".

Signed and Sealed this
Sixteenth Day of December, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,697,420 B2
APPLICATION NO. : 12/992531
DATED : April 15, 2014
INVENTOR(S) : Choi et al.

Page 1 of 1

It is certified that error appears in the above-identified patent and that said Letters Patent is hereby corrected as shown below:

On the Title Page

Item (12) Delete "Choi, I et al." and insert with -- Choi et al. --

Item (75) Inventors, please correct the name of the inventor from:

Dong Woon Cho. I to

Dong Woon Choi

Signed and Sealed this
Twenty-sixth Day of May, 2015

Michelle K. Lee
*Director of the United States Patent and Trademark Office*

UNITED STATES PATENT AND TRADEMARK OFFICE
CERTIFICATE OF CORRECTION

PATENT NO. : 8,697,420 B2  Page 1 of 1
APPLICATION NO. : 12/992531
DATED : April 15, 2014
INVENTOR(S) : Cho et al.

It is certified that error appears in the above-identified patent and that said Letters Patent is hereby corrected as shown below:

On the Title Page

Item (12) Delete "Choi, I et al." and insert with -- Cho et al. --

Item (75) Inventors, please correct the name of the inventor from:

Dong Woon Cho. I to

Dong Woon Cho

This certificate supersedes The Certificate of Correction issued May 26, 2015.

Signed and Sealed this
Twenty-fifth Day of August, 2015

Michelle K. Lee
*Director of the United States Patent and Trademark Office*